United States Patent
Hall et al.

(10) Patent No.: US 11,224,370 B2
(45) Date of Patent: Jan. 18, 2022

(54) IN-TOILET URINALYSIS SYSTEM WITH CAPILLARY DISPENSER

(71) Applicants: David R. Hall, Provo, UT (US); Dan Allen, Springville, UT (US)

(72) Inventors: David R. Hall, Provo, UT (US); Dan Allen, Springville, UT (US)

(73) Assignee: Hall Labs LLC, Provo, UT (US)

( * ) Notice: Subject to any disclaimer, the term of this patent is extended or adjusted under 35 U.S.C. 154(b) by 223 days.

(21) Appl. No.: 15/414,197

(22) Filed: Jan. 24, 2017

(65) Prior Publication Data

US 2018/0206772 A1 Jul. 26, 2018

(51) Int. Cl.
*A61B 5/20* (2006.01)
*G01N 33/493* (2006.01)
*A61B 10/00* (2006.01)
A61B 5/145 (2006.01)
A61B 5/1477 (2006.01)
A61B 5/1455 (2006.01)

(52) U.S. Cl.
CPC .............. *A61B 5/201* (2013.01); *A61B 5/207* (2013.01); *A61B 10/007* (2013.01); *G01N 33/493* (2013.01); *A61B 5/1455* (2013.01); *A61B 5/1477* (2013.01); *A61B 5/14507* (2013.01); *A61B 2562/0271* (2013.01); *A61B 2562/0295* (2013.01)

(58) Field of Classification Search
CPC ... A61B 5/201; A61B 5/1455; A61B 5/14507; A61B 10/007; A61B 5/1477; A61B 2562/0271; A61B 2562/0295; A61B 5/207; G01N 33/493
See application file for complete search history.

(56) References Cited

U.S. PATENT DOCUMENTS 3,466,145 A * 9/1969 Van Duyne .......... A61B 10/007
422/566
4,961,431 A * 10/1990 Ikenaga ............. A61B 5/14507
600/573
6,151,110 A * 11/2000 Markart ............. G01N 21/8483
356/244

(Continued)

OTHER PUBLICATIONS

"How to make Minor Adjustments to Your Toilet at The Home Depot". Screenshot of webpage on Nov. 13, 2014, accessed online. <https://web.archive.org/web/20141113025839/https://www.homedepot.com/c/minor_toilet_repair_adjust_toile_lift_chains_HT_PG_PL>.(Year: 2018).*

(Continued)

*Primary Examiner* — Matthew Kremer
*Assistant Examiner* — Samuel C Kim (57) ABSTRACT

We disclose an in-toilet urinalysis system which includes a system for collection urine and applying the urine to a urine test strip. The system may include an orifice within a toilet bowl which leads into a channel. The channel may be connected to a capillary which has an orifice at each end. Urine may pass through the orifice, into the channel, then may be moved by capillary action through the capillary. A urine test strip dispenser may move reaction pads on a urine test strip to the distal end of the capillary to load the reaction pads with urine. The reaction pads may absorb the urine from the most distal orifice of the capillary. A measurable chemical reaction may occur in the reaction pads in response to urine analytes.

10 Claims, 8 Drawing Sheets

(56) References Cited

U.S. PATENT DOCUMENTS

| | | | | |
|---|---|---|---|---|
| 2006/0184064 | A1* | 8/2006 | Paasch | A61B 10/007 600/573 |
| 2007/0093728 | A1* | 4/2007 | Douglas | A61B 5/157 600/583 |
| 2007/0246485 | A1* | 10/2007 | Mathew | B65B 69/005 222/213 |
| 2013/0158514 | A1* | 6/2013 | Elia | A61B 5/036 604/516 |
| 2015/0342574 | A1* | 12/2015 | Hall | A61B 10/007 600/573 |
| 2017/0284925 | A1* | 10/2017 | Spangenberg | A61B 10/007 |

OTHER PUBLICATIONS

Capillary. Merriam-Webster.com. Retrieved Apr. 16, 2019 from www.merriam.webster.com/dictionary/capillary (Year: 2019).*

"Track". Dictionary.com. 2020. Retrieved Apr. 14, 2020, from www.dictionary.com (Year: 2020).*

* cited by examiner

IN-TOILET URINALYSIS SYSTEM WITH CAPILLARY DISPENSER

BACKGROUND

Field of the Invention

This disclosure relates to devices and methods for analyzing urine samples to assess health status and diagnose disease.

Background of the Invention

Laboratory tests, including analysis of urine analytes, can be inconvenient and require a user to visit a healthcare facility. In the case or urinalysis, the collection process in a specimen cup or test strip on which a user may urinate directly may be unsanitary resulting in spilled or dripped urine. A convenient and simple device for collecting and analyzing urine is needed. A device which may be used in a user's home without the need to visit a healthcare facility is even more desirable.

BRIEF SUMMARY OF THE INVENTION

We disclose an in-toilet urinalysis system which uses urine test strips to detect analytes in a user's urine. To use the disclosed system, a user may urinate normally into a toilet bowl. The urine may enter an orifice in the toilet bowl which is above the standing water level in the toilet bowl. The orifice may lead into a channel and the channel may lead into a capillary. Both the channel and the capillary may be open at both ends and connect to each other end-to-end.

A urine test strip dispenser may place a urine test strip adjacent to the distal opening of the capillary. The urine test strip may include reaction pads which are cut on one or more sides to increase absorbency. The cut edge may wick urine into the test strip. A reagent in the reaction pad may conduct a chemical reaction which detects a urine analyte. The urine test strip dispenser may move the urine test strip laterally placing a second reaction pad adjacent to the distal opening of the capillary. The second reaction pad may wick urine into the absorbent material and conduct a chemical reaction to detect a second urine analyte. This process may be repeated to collect measurements of multiple urine analytes.

The disclosed in-toilet urinalysis system may include a reservoir which impedes the flow of urine so that urine more readily flows into the orifice. Some embodiments include mechanisms for detecting the presence of urine in the system and for performing optical measurements on urine in the system. Some embodiments of the disclosed in-toilet urinalysis system include a mechanism for flushing rinse water through the orifice, channel, and the capillary, then using a test strip to detect residual urine. Some embodiments include a slit-shaped opening to collect a second sample of urine for additional analysis.

DETAILED DESCRIPTION OF THE INVENTION

Definitions

Toilet, as used herein, means a device that collects biological products of a mammal, including urine and feces.

User, as used herein, means any mammal, human or animal, from which a urine sample is deposited into the in-toilet urinalysis system disclosed herein and analyzed.

Reaction pad, as used herein. means a section of a test strip which comprises absorbent material which includes a reagent that participates in a chemical reaction in the presence of a specific analyte. The chemical reaction produces a detectable product. Reaction pads may be comprised of enzyme paper. However, enzymes may or may not be present in the reaction pad.

Slit-shaped opening, as used herein, means an orifice with a length that is at least three times its width.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose a medical toilet which includes an in-toilet urinalysis system. The urinalysis system may be used to measure urine analytes using urine test strips. The urine test strips may be flushable urine test strips as disclosed in U.S. patent application Ser. No. 15/398,052 filed on Jan. 4, 2017 which is hereby incorporated by reference in its entirety. While the disclosed in-toilet urinalysis system may be used with other test strips, the flushable test strips in the referenced U.S. patent application are particularly useful. This is at least because the flushable test strips are configured to be loaded with urine on the cut sides of the reaction pads which are more absorbent than the top sides which may be slightly hydrophobic.

The toilet in which the disclosed in-toilet urinalysis system may resemble a traditional toilet. A user may urinate normally into the toilet without collecting urine in a specimen cup or urinating directly onto a test strip as is required for many other urinalysis systems. The toilet bowl of the disclosed in-toilet urinalysis system may include an inner wall and standing water level, similar to traditional toilets. However, the toilet bowl may include an orifice which is positioned above the standing water level. A portion of a urine stream from a user may enter the orifice for collection and analysis.

The orifice may be connected to a channel which includes a first end and a second end, both of which may be open for fluid flow. The first end may define the orifice. The channel may be in fluid connection with a capillary at a proximal end of the capillary. Consequently, urine flowing into the reservoir may flow into the orifice leading into the channel and into the capillary. The capillary may include an opening at a distal end for dispensing urine onto a reaction pad on a urine test strip.

The channel and capillary may be positioned in a captive volume which may be either within or outside of and adjacent to the toilet bowl. This presence of the captive volume creates a space for other components of the disclosed in-toilet urinalysis system. The captive volume may be sealed to prevent toilet water from entering the captive volume. In some of embodiments, a fluid resistant seal may surround the channel. This is useful because the orifice is within the toilet bowl above the standing water line to collect urine and, in some embodiments, the channel may lead through the toilet water, through an opening, and into the captive volume. The fluid resistant seal may prevent toilet water from leaking through the opening into the captive volume.

The disclosed in-toilet urinalysis system may further include a urine test strip dispenser which may also be positioned within the captive volume. The urine test strip dispenser may position a urine test strip adjacent to the opening at the distal end of the capillary. The reaction pad may wick the urine from the distal opening of the capillary into a reaction pad. When using the flushable test strips disclosed in U.S. patent application Ser. No. 15/398,052, the urine test strip dispenser may position the cut side of the reaction pad which is more absorbent than the top surface nearest the opening at the distal end of the capillary.

The urine test strip dispenser may move the urine test strip to be positioned adjacent to the opening in the distal end of the capillary. The urine test strip dispenser may repeatedly move the test strip laterally and repeatedly move a reaction pad toward the opening in the distal end of the capillary. Consequently, in this embodiment, reaction pads are sequentially loading with urine.

In some embodiments, the urine test strip dispenser may include a track and a plurality of grip rollers. The urine test strip may be stored in a cartridge and grip rollers may advance the urine test strip as it is pulled out of the cartridge and advanced along a track. The grip rollers may be advanced by a motor connected to a belt.

In other embodiments, the urine test strip dispenser may include a solenoid. Again, the urine test strip may be stored in a cartridge. The urine test strip may be pulled out of the cartridge and onto a track. The solenoid may extend and push the track laterally past the opening in the distal end of the capillary while reagent pads are sequentially loaded.

In some embodiments, the track and a plurality of grip roller system disclosed above may be used in combination with a solenoid. The track and grip roller system may move the test strip laterally as described above. The solenoid may be positioned perpendicular to the track. When extended, the solenoid may push the track, with the test strip inside it, towards the capillary. A reaction pad may absorb urine from the capillary. The solenoid may then retract and move the track away from the capillary. The motor and grip rollers may advance the track to the next reaction pad and repeat the process loading the next reaction pad.

In some embodiments, the disclosed in-toilet urinalysis system further includes a valve which may inhibit backflow of urine out of the system and inhibit further inflow of liquid during urinalysis. The valve may be a pinch valve, a solenoid valve, or other valve known in the art. In some embodiments of the disclosed in-toilet urinalysis system, including those which include a valve, the channel may include a compliant material. In embodiments which include a pinch valve, the pinch valve may compress the channel causing the compliant material to constrict and close off the channel.

Some embodiments of the disclosed in-toilet urinalysis system may include mechanisms which detect the presence or absence of urine in the system. Some embodiments may include a temperature sensor which measures the temperature within either the channel or the capillary. The temperature sensor may be in electrical connection with a controller. Because urine is typically at least body temperature, the controller may identify the presence of urine receiving an elevated temperature reading from the temperature sensor.

In other embodiments, the channel or capillary may include one or more optical windows. An optical sensor within the in-toilet urinalysis system may analyze the contents of the channel or capillary by measuring optical density.

The optical sensor may be in electrical connection with a controller. The controller may determine the presence of urine in the channel or capillary based on the optical density reading received from the optical sensor.

In some embodiments, the optical windows in the channel or capillary and the optical sensor may analyze the urine providing data in addition to that collected by the urine test strips. For example, urine specific gravity and color may be determined using the optical sensor. In some embodiments, reagents may be added to the urine sample through the channel. These reagents may be used to detect properties and analytes in a urine sample followed by spectral analysis. In some embodiments, reagents may be used which do not interfere with urine test strip chemistry. In other embodiments, reagents may be added and spectral analysis conducted using remaining urine after the urine test strip has been loaded.

Some embodiment may further include a reservoir which may temporarily impede the flow of urine as a user's urine stream flows over it. The reservoir may be elevated to stand above the standing water level in the toilet bowl so that toilet water does not mix with the urine sample as it is collected. The reservoir may be tilted so that urine flows across the reservoir and into the toilet water. In some embodiments, the reservoir is tilted at an angle of equal or greater than 17 degrees. The reservoir may also have skirted sides fanning out from the reservoir so that urine which reaches the top of the reservoir may flow over the skirted sides into the toilet water. In some embodiments, the concave underside of the reservoir and the inner wall of the toilet bowl may define the captive volume which houses the channel, the capillary, the urine test strip dispenser, and, in some embodiments, other analytical devices disclosed herein.

In some embodiments, the reservoir may be elongated, resembling a shallow ravine, and include a first and second end. In some embodiments, the width of the first end may be wider than the width of the second end. In some embodiments, the width of the first end is at least double the width of the second end. In some embodiments, the width of the first end is at least three times the width of the second end. In some embodiment, first end is approximately circular and leads into a second end which is shaped like an elongated ravine. In the latter embodiment, the reservoir may be tilted downward from the first end to the second end allowing urine to flow from the first end to the second end and into the toilet water.

In some embodiments, the reservoir includes a temporary barrier which further impedes urine flow into the toilet water. The temporary barrier may be a gate which may be opened and closed. In some embodiments, the gate may be attached to the reservoir by one or more hinges. The gate may open when a volume of urine trapped in the reservoir builds up on one side of the gate and applies force to the gate. When enough force is applied to the gate, it may open and release the urine to flow out of the reservoir into the toilet water.

In some embodiments, the disclosed in-toilet urinalysis system includes a slit-shaped opening which, in addition to the orifice described herein, may collect urine for analysis. The slit-shaped opening may deliver urine to a device which may perform a chemical analysis of the urine sample. The device may perform analyses other than those conducted by the urine test strip. The slit-shaped opening may be a component of a urine sampling system as disclosed in U.S. patent application Ser. No. 15/383,187 filed on Dec. 19, 2016 which is hereby incorporated by reference in its entirety.

Some embodiments of the disclosed in-toilet urinalysis system include a system for cleaning out the system between uses. In some embodiments, after analyzing a urine sample, the toilet may flush and rinse water may enter the orifice. The rinse water may follow the same path as the urine sample by traveling through the channel and through the capillary. In some embodiments, an absorbent material may be placed adjacent to the distal opening of the capillary to wick remaining urine and a volume of rinse water. A urine test strip dispenser may move a urine test strip that is designed to test the cleansing process up to the capillary. The reaction pads of this urine test strip may include a reagent which detects an analyte that is present in significant amounts in any user's urine. The urine test strip dispenser may place a reaction pad on this test strip adjacent to the distal opening of the capillary to wick a sample of fluid from the capillary. The reaction pad may conduct a chemical reaction to detect the urine analyte. If the urine analyte is present, a second sample of absorbent material may be placed adjacent to the distal opening of the capillary to wick more fluid out. The process may be repeated until the urine analyte is not detectable or is detectable below a defined level. The in-toilet urinalysis system is now ready for another use.

Figure 1:
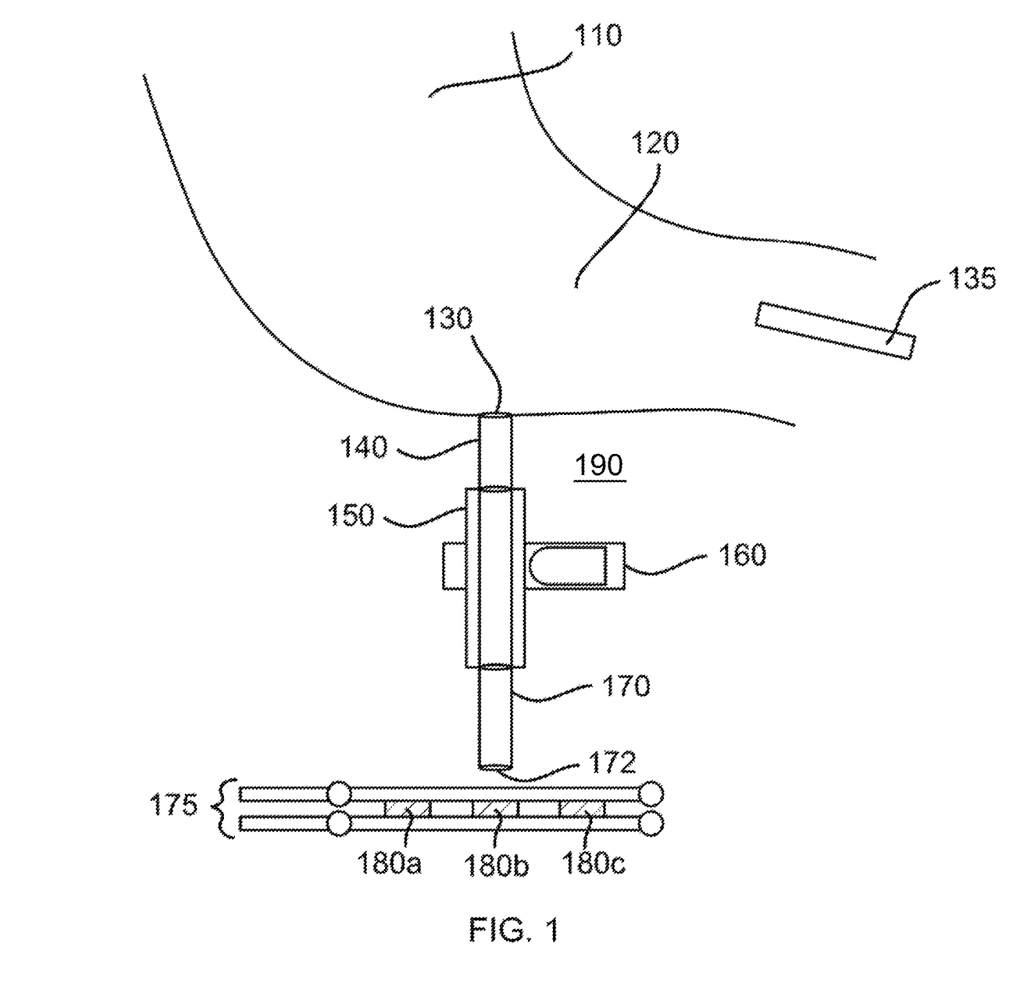
FIG. 1 is a cross-sectional view of an embodiment of the disclosed in-toilet urinalysis system.

Referring now to the drawings, FIG. 1 illustrates an embodiment of the disclosed in-toilet urinalysis system which is a cross section taken from within a toilet bowl. A first end 110 and a second end 120 of a reservoir are shown. In the embodiment of FIG. 1, first end 110 is wider than second end 120. The relative widths of first end 110 and second end 120, as illustrated, may not be proportional. A channel is shown which includes two sections. First section 140 is open at both ends and defines orifice 130. Orifice 130 leads into the reservoir within the toilet bowl and collects urine. Second section 150 of the channel is connected to first section 140. First section 140 may include a noncompliant material which may be stainless steel, polyvinyl chloride (PVC) pipe, or other noncompliant polymer. Second section 150 may include a compliant material which may be compliant rubber.

The embodiment shown in FIG. 1 includes pinch valve 160 which is shown in its open state. When actuated, pinch valve 160 may compress section 150 thereby closing off the path of fluid through the orifice and into the channel. An open end of second section 150 is connected to capillary 170. Capillary 170 includes distal opening 172. A user's urine stream may be temporarily collected in the reservoir and enter orifice 130. The urine may travel through first end 140 and second end 150 of the channel and into capillary 170. Urine test strip dispenser is shown below distal opening 172. The urine test strip dispenser includes track 175. The four circles on track 175 illustrate grip rollers. A test strip with reaction pads 180a, 180b, and 180c is loaded into track 175. Reaction pad 180b is shown adjacent to distal opening 172. The absorbent material in reaction pad 180b wicks urine from capillary 170 through distal opening 172. As track 175 moves the test strip laterally, an adjacent reaction pad will absorb urine from capillary 175. FIG. 1 also includes slit-shaped opening 135 which may collect urine for other analysis techniques.

Figure 2:
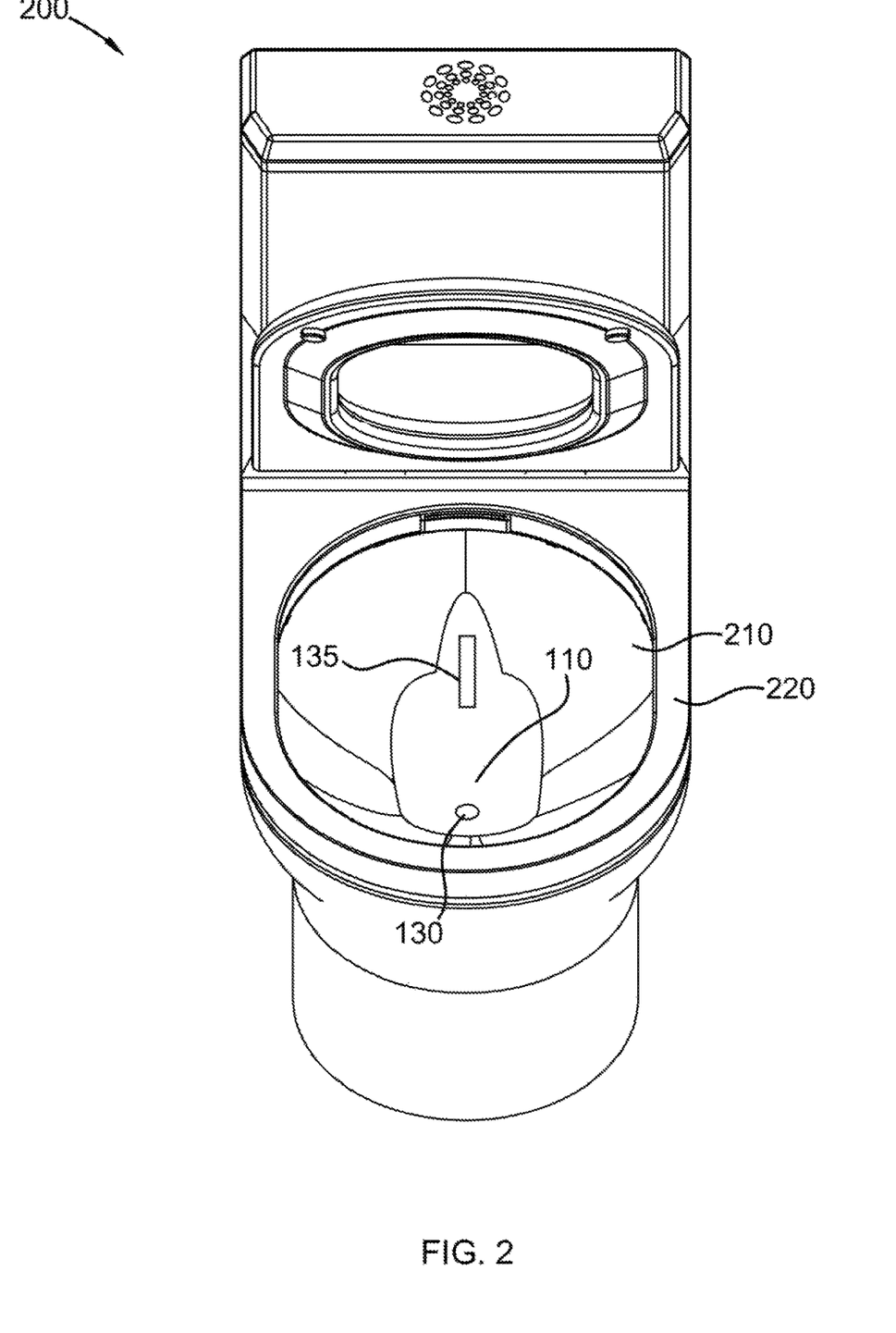
FIG. 2 is an aerial view of an embodiment of a toilet which includes the disclosed in-toilet urinalysis system.

FIG. 2 shows medical toilet 200 which is an embodiment of the disclosed in-toilet urinalysis system as viewed from above. Toilet 200 includes toilet bowl 210 and toilet seat 220. A reservoir is shown within toilet bowl 210 which includes first end 110 which is widened relative to the second end. Orifice 130 is shown at first end 110 and slit-shaped opening 135 is shown at the second end of the reservoir which is more narrow than first end 110.

Figure 3A:
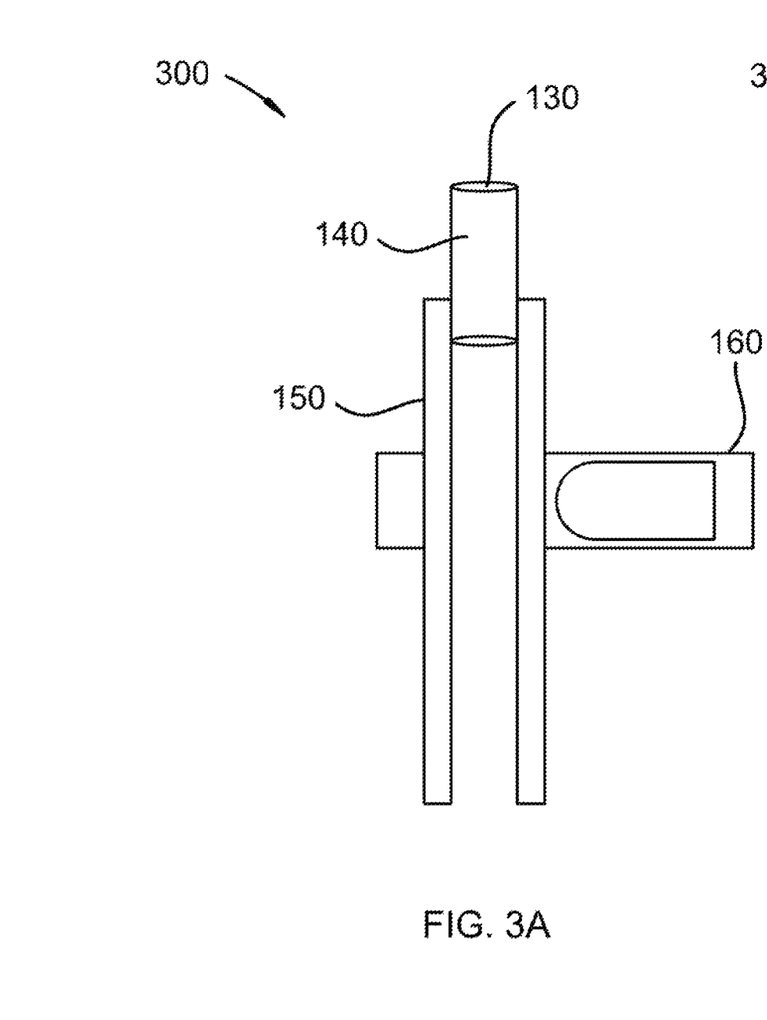
FIG. 3A is an embodiment of a channel within an embodiment of the disclosed in-toilet urinalysis system including a pinch valve which is open.
Figure 3B:
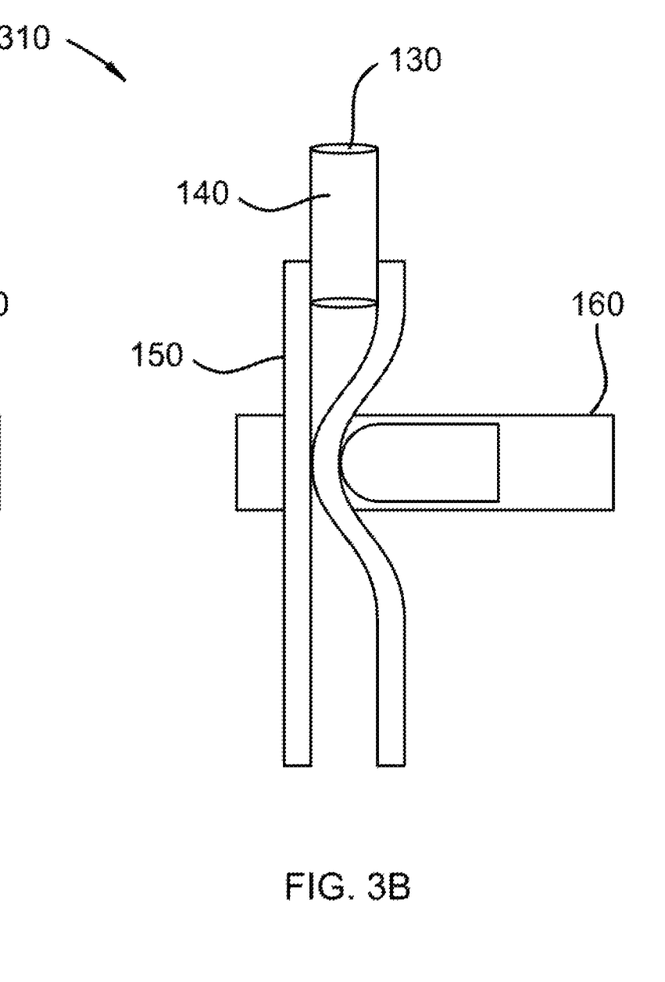
FIG. 3B is the embodiment of FIG. 3A in which the pinch valve is closed.

FIGS. 3A and 3B illustrate the channel with pinch valve 160. FIG. 3A illustrates open channel 300 which is an embodiment of the channel in its open position. As described with regard to FIG. 1, second section 150 of the channel includes compliant material. However, pinch valve 160 is not actuated so the compliant material is not compressed.

FIG. 3B shows closed channel 310 which is an embodiment of the channel in its closed position. Pinch valve 160 is actuated and has compressed the compliant material of second section 150 of the channel. Second section 150 is now closed and fluid flow from the toilet bowl is impeded. Fluid flow out of the channel is also impeded.

Figure 4A:
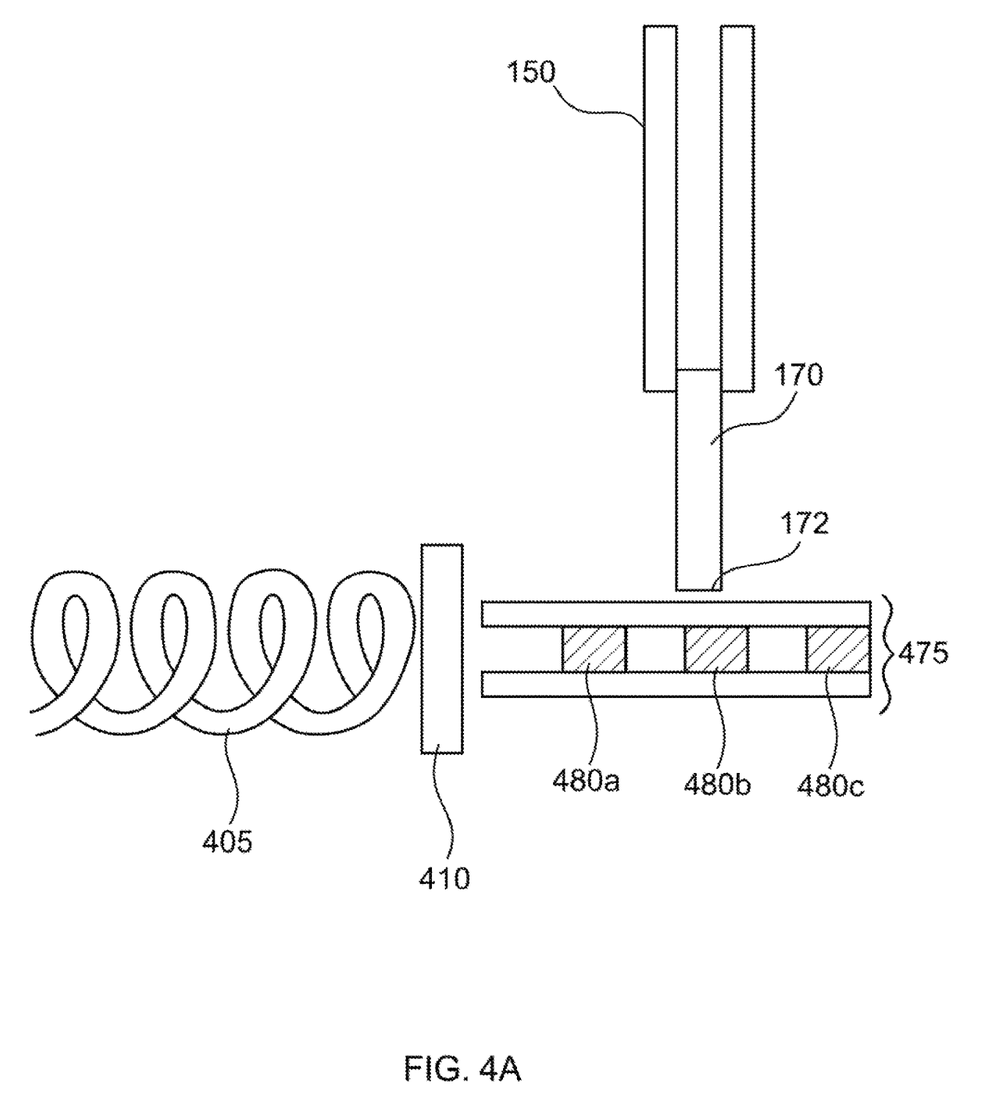
FIG. 4A is an embodiment of a portion of the in-toilet urinalysis system in which a solenoid moves the test strip past the capillary opening.

FIG. 4A includes an embodiment of a urine test strip dispenser which includes a solenoid. A urine test strip is loaded into track 475 and includes reaction pads 480a, 480b, and 480c. Track 475 is positioned below capillary 170. Solenoid 405 extends and applies force to plate 410. Plate 410 then applies force to track 475 and pushes it laterally past capillary 170. As shown in FIG. 4A, reaction pad 480b is directly below distal opening 172 of capillary 170. Urine is wicked into reaction pad 480b from distal opening 172. As solenoid 405 extends further, track 475 moves to the right on FIG. 4A so that reaction pad 480a is directly below distal opening 172 and urine is wicked into reaction pad 480a.

Figure 4B:
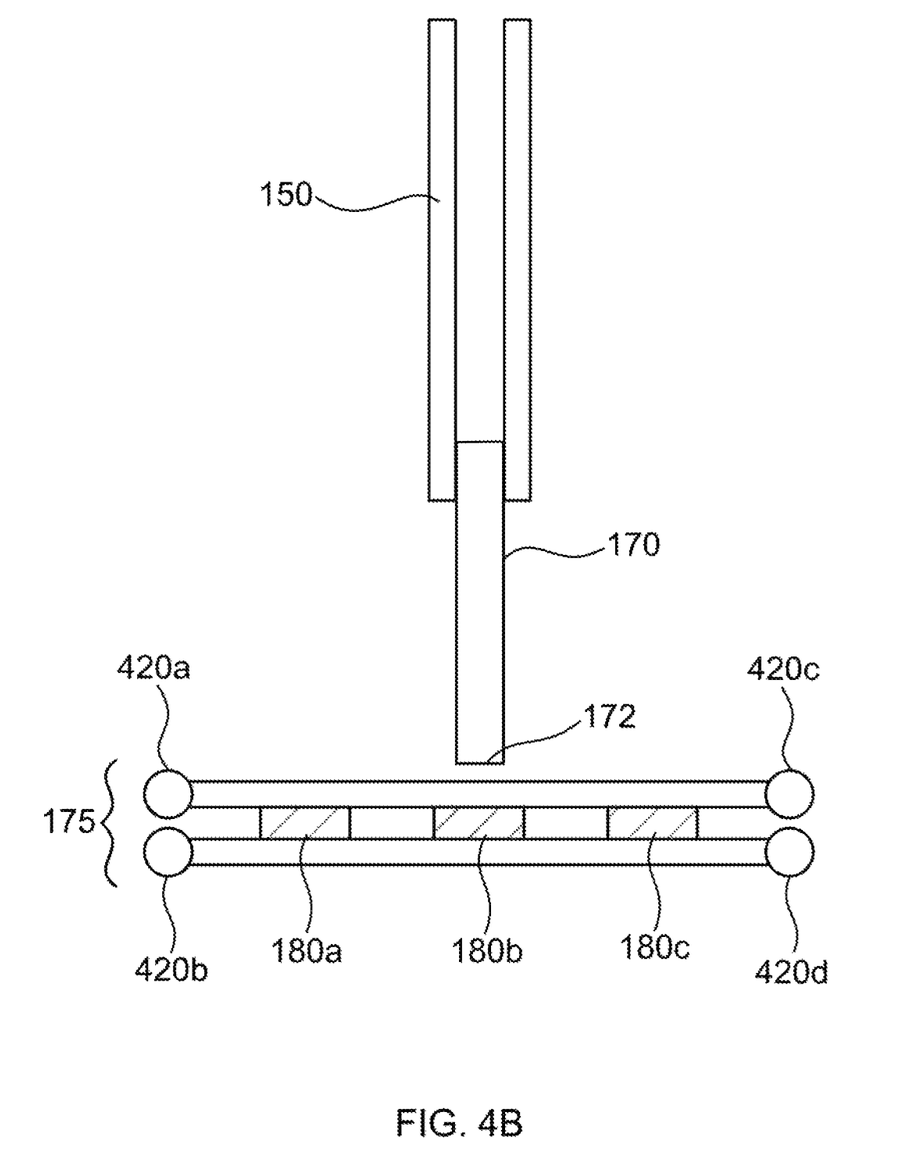
FIG. 4B is an embodiment of a portion of the in-toilet urinalysis system in which a track and grip rollers move the test strip past the capillary opening.

FIG. 4B illustrates the urine test strip dispenser 175 shown in FIG. 1 which includes track 175 and grip rollers 420a, 420b, 420c, and 420d. A urine test strip is loaded into track 175 and includes reaction pads 180a, 180b, and 180c. A motor causes grip rollers 420a, 40b, 420c, and 420d to rotate and move the track 175 laterally. As illustrated in FIG. 4B, reaction pad 180b is directly below distal opening 172 of capillary 170. The absorbent material of reaction pad 180b will wick urine from distal opening 172. The urine test strip will then be moved laterally placing another reaction pad under distal opening 172 to be loaded with urine.

Figure 5:
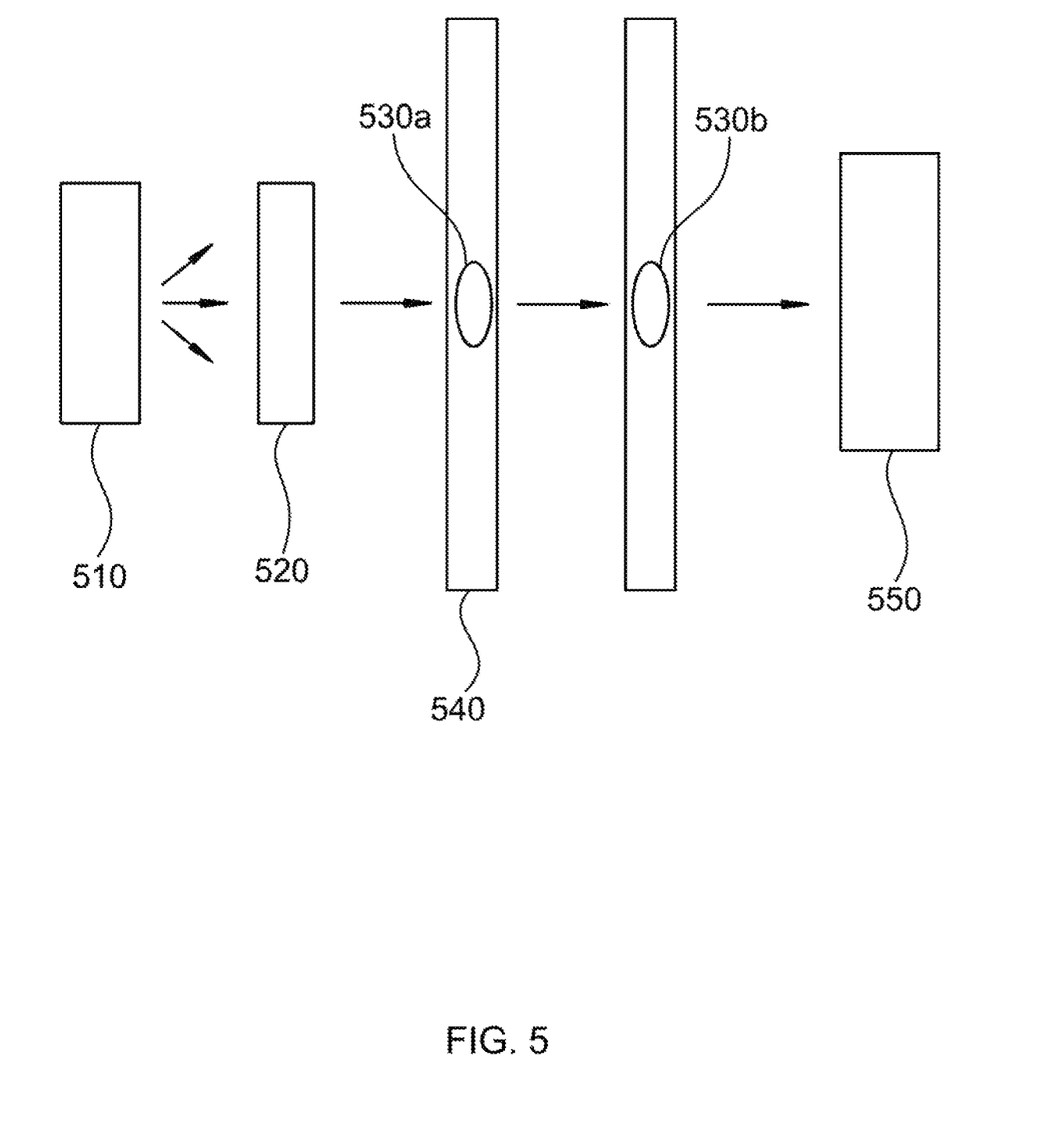
FIG. 5 is an embodiment of a channel within an embodiment of the disclosed in-toilet urinalysis system which includes optical windows and an optical sensor.

FIG. 5 illustrates channel 540 which includes optical windows 530a and 530b. The embodiment of the channel shown in FIG. 5 may be used to detect the presence of urine by measuring the optical density of the contents of channel 540. It may also be used to analyze urine. For example, urine specific gravity may be determined using the embodiment shown in FIG. 5.

Referring again to FIG. 5, light source 510 emits light with varied wavelengths as shown by the three arrows pointing in different directions. The light passes through filter 520 which blocks all but one or a range of wavelengths of light as shown by the single horizontal arrow. The light sequentially passes through optical window 530a, the contents of channel 540, and optical window 530b. Light emitted from optical window 530b is detected by optical sensor 550.

Figure 6:
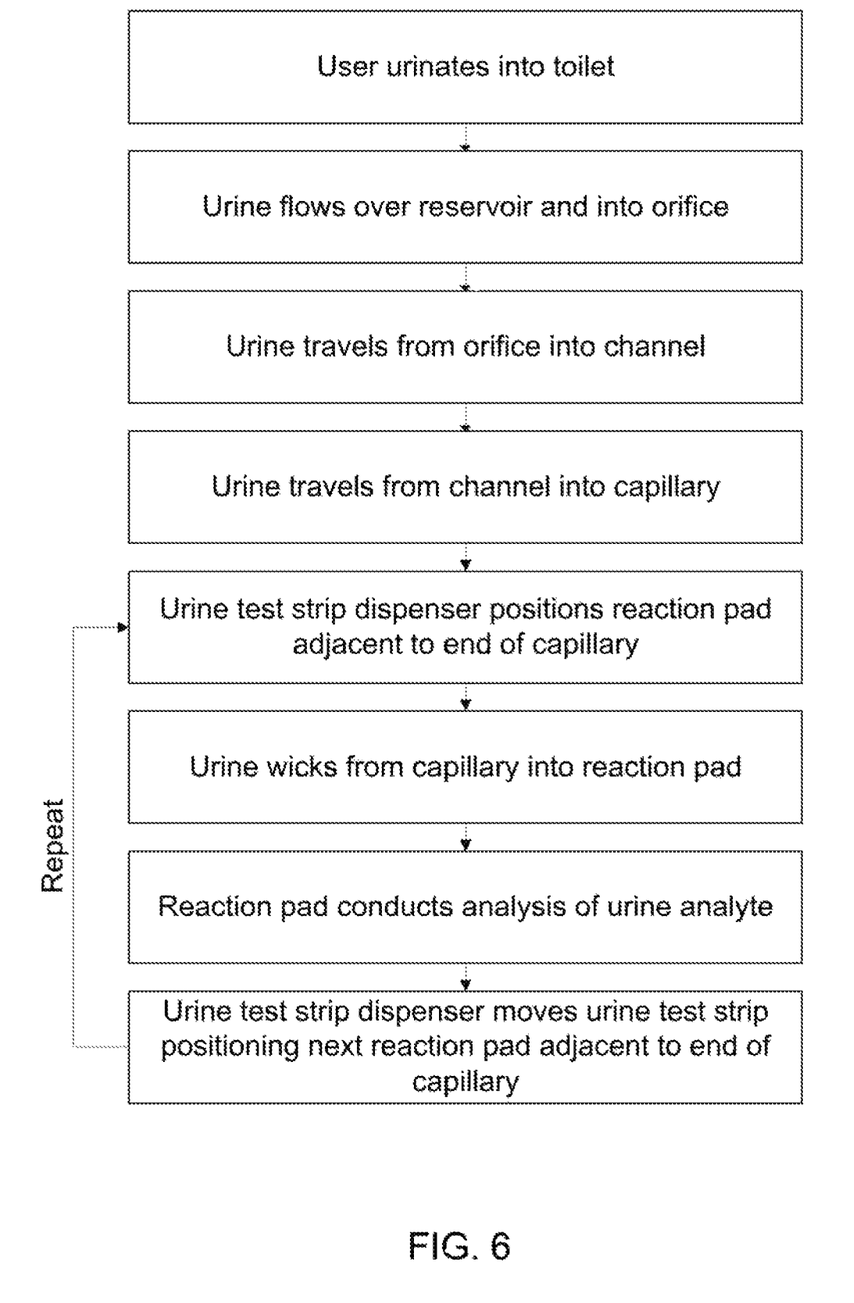
FIG. 6 is a flow chart illustrating steps which may be taken to analyze a urine sample using the disclosed in-toilet urinalysis system.

FIG. 6 is a flow chart describing steps which may be taken when using the disclosed in-toilet urinalysis system. As described in FIG. 6, a user urinates into the toilet. Urine flows over a reservoir in the toilet bowl and into the orifice. Urine travels through the orifice, through the channel, and into the capillary. A urine test strip dispenser positions a test strip with reaction pads below the capillary. The test strip dispenser sequentially places each reaction pad adjacent to the distal opening of the capillary. The absorbent material in the reaction pad wicks urine into the reaction pad for analyte detection. The urine test strip dispenser then moves the urine test strip placing an adjacent reaction pad adjacent to the distal opening of the capillary to wick urine into the adjacent reaction pad and conduct a chemical reaction to detect a urine analyte.

Figure 7:
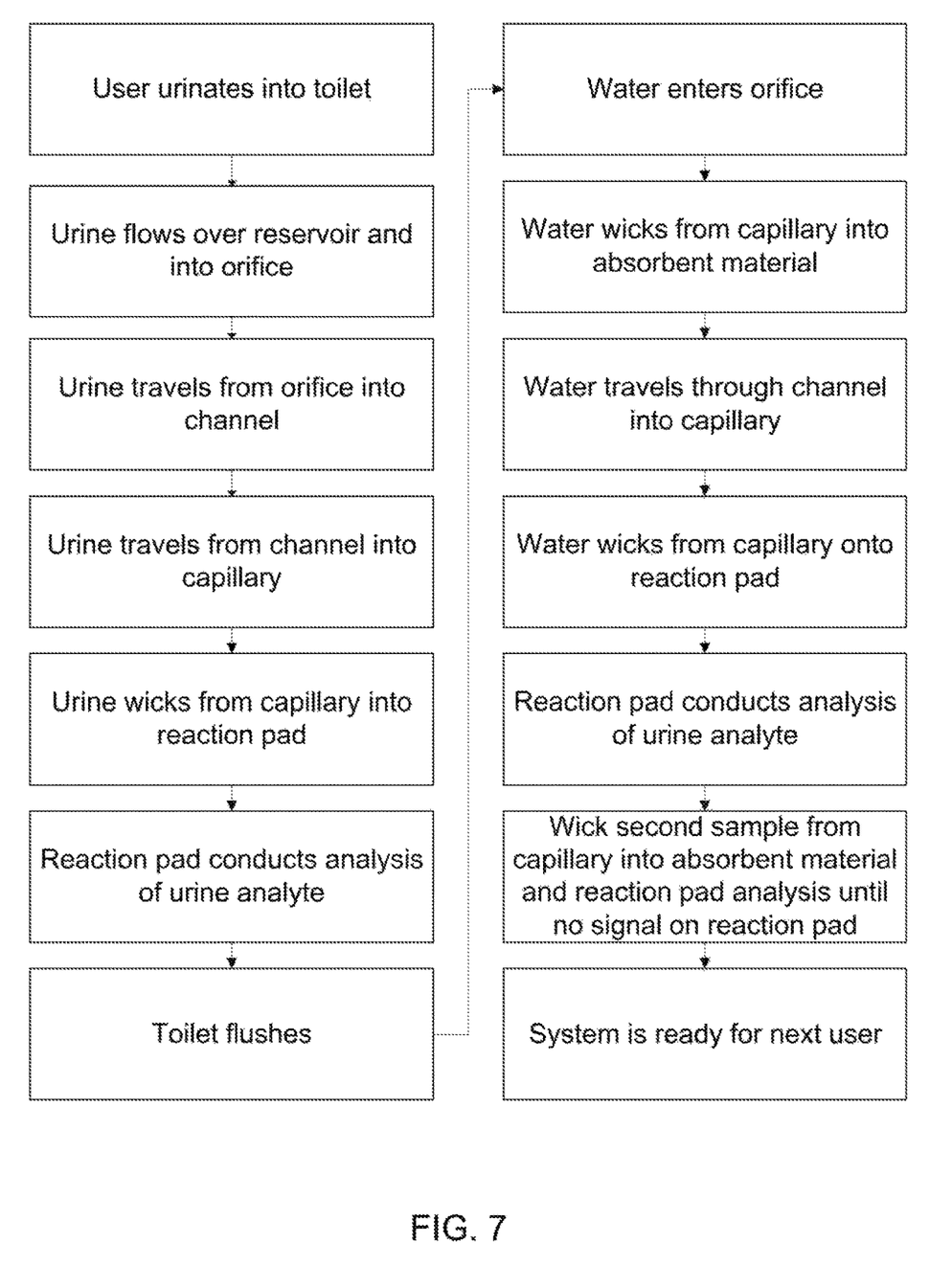
FIG. 7 is a flow chart illustrating steps which may be taken to analyze a urine sample with the disclosed in-toilet urinalysis system then clean the system between uses.

FIG. 7 is a flow chart illustrating steps that may be taken to clean the in-toilet urinalysis system between uses. The user urinates into the toilet and urine travels through the system as described with regard to FIG. 6. The final reaction pad wicks urine from the distal opening of the capillary and conducts a chemical reaction to detect a urine analyte. The toilet then flushes and moves the urine in the toilet bowl into the sewer system. This time, rinse water enters the orifice, travels through the channel into the capillary. In doing so, residual urine is flushed through the in-toilet urinalysis system. An absorbent material is placed adjacent to the distal opening of the capillary to wick out rinse water and residual urine. In some embodiments, the test strip dispenser may include a section of the absorbent material and place the absorbent material adjacent to the capillary. A urine test strip dispenser places a test strip which is designed to detect urine of any kind adjacent to the distal opening of the capillary. The reaction pads of this test strip may include reagents that detect an analyte that is present in detectable amounts in any user's urine. The first reaction pad wicks fluid from the capillary and is detected. If urine is detected, the urine test strip dispenser moves the test strip laterally so that a second section of absorbent material is placed adjacent to the distal opening of the capillary. A reaction pad again tests for residual urine. The process is repeated until a reaction pad indicates that the signal for the urine analyte is not detectable or is below a defined level. The system is ready for the next user.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. An in-toilet urinalysis system comprising:
 a toilet bowl comprising:
  an inner wall;
  a standing water level in the toilet bowl;
  a reservoir for temporarily impeding urine flow, wherein the reservoir comprises a first end and a second end, wherein the first end of the reservoir comprises a first width, wherein the second end of the reservoir comprises a second width, and wherein the first end of the reservoir is higher than the second end of the reservoir;
  a slit-shaped opening disposed within the reservoir collecting a first urine sample, wherein a length of the slit-shaped opening is perpendicular to the second width of the reservoir, and wherein the slit-shaped opening is in fluid connection with an analyzer configured to perform a chemical analysis of the first urine sample; and
  an orifice within the reservoir, wherein the orifice is above the standing water level and is configured to collect a second urine sample;
 a captive volume within or adjacent to the toilet bowl, wherein the captive volume is sealed from toilet water entry, wherein the following are housed within the captive volume:
  a channel comprising a first end in fluid connection with a second end, wherein the first end of the channel defines the orifice, and wherein the channel extends into the captive volume;
  a capillary comprising a proximal opening and a distal opening, wherein the proximal opening is in fluid connection with the second end of the channel and wherein capillary action causes urine from the second urine sample to move through the capillary and remain at the distal opening; and
  a urine test strip dispenser comprising a track, a cartridge, and grip rollers, wherein the grip rollers is configured to remove a urine test strip from the cartridge and load the urine test strip into the track, and the track holding the urine test strip is configured to be then positioned so that a reaction pad of the urine test strip is adjacent to the distal opening of the capillary such that the reaction pad wicks the urine from the distal opening of the capillary into the reaction pad;
 wherein the reservoir stands above the standing water level and wherein an underside of the reservoir and the inner wall of the toilet bowl define the captive volume.

2. The in-toilet urinalysis system of claim 1, wherein the reservoir is elongated and tilted at an angle of equal to or greater than 17 degrees about a horizontal plane.

3. The in-toilet urinalysis system of claim 1, wherein the channel comprises a compliant material.

4. The in-toilet urinalysis system of claim 1, further comprising a valve in connection with the channel, wherein the valve, when actuated, prevents fluid flow through the channel.

5. The in-toilet urinalysis system of claim 4, wherein the valve is selected from the following: a pinch valve and a solenoid valve.

6. The in-toilet urinalysis system of claim 1, further comprising a temperature sensor, wherein the temperature sensor is in thermal connection with the channel, the capillary, or both the channel and the capillary.

7. The in-toilet urinalysis system of claim 6, wherein the temperature sensor is in electronic communication with a controller, and wherein the controller is configured to identify a presence of the urine from the second urine sample in the channel or the capillary based on a minimum temperature.

8. The in-toilet urinalysis system of claim 1, further comprising:
   at least one optical window, wherein the at least one optical window is positioned in either the channel or the capillary; and
   an optical sensor in electromagnetic communication with the at least one optical window, wherein the optical sensor is configured to analyze the second urine sample through the at least one optical window.

9. The in-toilet urinalysis system of claim 8, wherein the optical sensor is in electronic communication with a controller, wherein the controller is configured to determine a presence of the urine from the second urine sample in the channel or the capillary based on optical density.

10. The in-toilet urinalysis system of claim 1, wherein the urine test strip dispenser further comprises a motor, wherein the grip rollers comprise at least two grip rollers and the motor is connected to the at least two grip rollers, wherein the motor is configured to rotate the at least two grip rollers, wherein the track is positioned between the at least two grip rollers, and wherein the track is configured to be moved past the distal opening of the capillary as the at least two grip rollers rotate.

* * * * *